(12) United States Patent
Ardizzone

(10) Patent No.: US 6,626,820 B1
(45) Date of Patent: Sep. 30, 2003

(54) MAGNETIC MATTRESS PAD

(75) Inventor: Vincent Ardizzone, Port Jefferson, NY (US)

(73) Assignee: Nu-Magnetics, Inc., Port Jefferson, NY (US)

(*) Notice: Subject to any disclaimer, the term of this patent is extended or adjusted under 35 U.S.C. 154(b) by 0 days.

(21) Appl. No.: 10/136,894

(22) Filed: Apr. 29, 2002

Related U.S. Application Data

(63) Continuation-in-part of application No. 10/004,143, filed on Oct. 23, 2001, which is a division of application No. 09/379,826, filed on Aug. 23, 1999, now Pat. No. 6,322,491, which is a continuation-in-part of application No. 09/038,508, filed on Mar. 10, 1998, now abandoned, which is a continuation-in-part of application No. 08/911,950, filed on Aug. 15, 1997, now Pat. No. 6,293,900, which is a continuation-in-part of application No. 08/678,348, filed on Jul. 11, 1996, now Pat. No. 5,871,438, which is a continuation of application No. 08/573,390, filed on Dec. 15, 1995, now Pat. No. 5,538,495, which is a continuation of application No. 08/427,733, filed on Apr. 24, 1995, now Pat. No. 5,514,072, which is a continuation of application No. 08/276,876, filed on Jul. 18, 1994, now abandoned, which is a continuation of application No. 08/158,607, filed on Nov. 29, 1993, now abandoned, which is a continuation of application No. 07/990,927, filed on Dec. 14, 1992, now Pat. No. 5,277,692, which is a continuation of application No. 07/823,149, filed on Jan. 21, 1992, now abandoned, said application No. 10/136,894, is a continuation-in-part of application No. 09/999,884, filed on Oct. 31, 2001.

(60) Provisional application No. 60/287,253, filed on Apr. 27, 2001.

(51) Int. Cl.[7] .......................... A61N 1/00; A47C 17/00
(52) U.S. Cl. ................................................ 600/15; 5/693
(58) Field of Search ............................ 600/9, 13–15, 600/26; 5/693, 736, 406, 451, 701; 128/798, 799

(56) References Cited

U.S. PATENT DOCUMENTS

| 4,143,435 A | * | 3/1979 | Masuda | 5/693 |
| 4,924,542 A | * | 5/1990 | Yamaguchi | 5/693 |

* cited by examiner

Primary Examiner—Eric F. Winakur
Assistant Examiner—Nikita R Veniaminov
(74) Attorney, Agent, or Firm—Cislo & Thomas LLP

(57) ABSTRACT

A magnetic mattress pad comprising an uppermost portion, an upper portion, a lower portion and alternating magnetic means for providing changes in magnetic polarity. The alternating magnetic means are disposed in cavities in the upper portion and the lower portion, but the alternating magnetic means are not located in the uppermost portion. The alternating magnetic means comprises a plurality of continuous, or uni-pole, magnets and a plurality of triangularboard button magnets. The plurality of uni-pole magnets are distributed in an asymmetrical fashion and the plurality of triangularboard button magnets are located only in the upper portion whereby the magnetic mattress pad provides highly magnetic magnetotherapy while one rests or sleeps.

13 Claims, 4 Drawing Sheets

MAGNETIC MATTRESS PAD

CROSS-REFERENCES TO RELATED APPLICATIONS

This application is a continuation-in-part of U.S. patent application Ser. No. 10/004,143 entitled Flexible Magnetic Insole and Method of Manufacture which was filed on Oct. 23, 2001;

which application is a divisional application of U.S. patent application Ser. No. 09/379,826 filed Aug. 23, 1999, for a Flexible Magnetic Insole and Method of Manufacture, now U.S. Pat. No. 6,322,491 issued Nov. 27, 2001;

which application is a continuation-in-part application of U.S. patent application Ser. No. 09/038,508 filed Mar. 10, 1998 entitled Magnetic Wrap for Joints now abandoned;

which application is a continuation-in-part of U.S. patent application Ser. No. 08/911,950 filed Aug. 15, 1997 entitled Magnetic Face Mask which issued as U.S. Pat. No. 6,293,900 on Sep. 25, 2001;

which application is a continuation-in-part application of U.S. patent application Ser. No. 08/678,348 filed Jul. 11, 1996 entitled Flexible Magnetic Pad with Multi-Directional Constantly Alternating Polarity Zones which issued as U.S. Pat. No. 5,871,438 on Feb. 16, 1999;

which application is a continuation of application Ser. No. 08/573,390 filed Dec. 15, 1995 entitled Flexible Magnetic Pad with Multi Directional Constantly Alternating Polarity Zones which issued as U.S. Pat. No. 5,538,495 on Jul. 23, 1996;

which application is a continuation of application Ser. No. 08/427,733, filed Apr. 24, 1995 entitled Flexible Magnetic Pad with Multi Directional Constantly Alternating Polarity Zones, now U.S. Pat. No. 5,514,072 issued May 7, 1996;

which application is a continuation of application Ser. No. 08/276,876, filed Jul. 18, 1994, now abandoned;

which application is a continuation of application Ser. No. 08/158,607, filed Nov. 29, 1993, now abandoned;

which application is a continuation of application Ser. No. 07/990,927, filed Dec. 14, 1992 entitled Flexible Magnetic Pad With Multi-Directional Constantly Alternating Polarity Zones, now U.S. Pat. No. 5,277,692 which issued on Jan. 11, 1994;

which application is a continuation of application Ser. No. 07/823,149, filed Jan. 21, 1992, now abandoned.

This application is related to U.S. provisional patent application Ser. No. 60/287,253 filed Apr. 27, 2001 for a Magnetic Insole and Method of Manufacture.

This application is related to U.S. patent application Ser. No. 08/565,826 filed Dec. 1, 1995 entitled Magnetic Body Brace, now abandoned.

This application is a continuation-in-part of patent application Ser. No. 09/999,884 filed on Oct. 31, 2001 entitled Magnetic Wrap for Joints;

which application is a continuation-in-part application of U.S. patent application Ser. No. 09/038,508 filed Mar. 10, 1998 entitled Magnetic Wrap for Joints, above.

The contents of all applications of which the present application is a divisional, continuation, continuation-in-part, or otherwise to which this application is related are incorporated herein by this reference thereto.

BACKGROUND OF THE INVENTION

1. Field of the Invention

This invention relates to magnetotherapeutic devices, and more particularly to a mattress pad incorporating static magnetic field generators in the form of magnets to provide magnetotherapy to adjacent-tissues.

2. Description of the Related Art

Magnetotherapy uses magnetic fields to provide therapeutic and restorative treatment to limbs, organs, and other parts of the body. Generally, one means by which magnetotherapy may be achieved is by bringing a magnet or a series of magnets into close proximity with the affected body part or organ of interest. Although there are many theories on how these magnets work to provide magnetic therapy, all involve Faraday's Law of Magnetic Induction. As is known according to Faraday's Law of Magnetic Induction, as well as the Hall Effect, charged particles experience; a force acting on them when they move through a magnetic field in a perpendicular direction. Since human blood is replete with ions and electrolytes, it has many charged molecules, particles, and the like which experience a force, including an aligning force, when moving through a magnetic field. When exposed and caused to so travel through a magnetic field, such ions and electrolytes may generate heat, causing the associated blood vessel to widen. The widening of the blood vessel would then allow increased volumes of blood to flow through the blood vessel.

Polar molecules (such as water) also respond to magnetic fields in a manner similar to that for charged molecules. Additional therapeutic or restorative effects might arise through the alignment of polar molecules as they pass through the magnetic field. When subject to a magnetic field, polar molecules rotate to align themselves with the field. Such alignment would alternate with the magnetic polarity as the polar molecules traveled through different regions of such magnetic polarity. The mechanical motion of the rotation of such polar molecules might also cause heating and the like and would also stimulate, mix, or agitate the blood in a gentle manner, causing it to gently churn. Such mixing of the blood at the molecular level may cause it to more easily recognize foreign matter. By recognizing foreign matter, the blood and/or immune system may be able to more readily address such foreign matter. There are also other theories of operation as well still under investigation.

Several patents are known having various designs for the alternation of magnets of different polarity to provide spatially diverse magnetic fields. The patent to Latzke (U.S. Pat. No. 4,489,711 issued Dec. 25, 1984) and the patents to Ardizzone (U.S. Pat. No. 5,277,692 issued Jan. 11, 1994; U.S. Pat. No. 5,514,072 issued May 7, 1996; and U.S. Pat. No. 5,538,495 issued Jul. 23, 1996) all disclose a variety of magnetic plaster and magnetic pads having certain magnetic geometries in order to achieve spatially varying magnetic fields through the use of magnets.

In the past, the only way to offer or provide both mechanical support and magnetic therapy was to insert magnets between a brace and the associated body joint. Recently, stronger static magnetic materials have become more readily available in the commercial market. Also, strong magnets were placed in mattresses or placed in bedding to provide a magnetic effect. Particularly, permanent magnets incorporating the element neodymium (atomic number 60) provide strong magnetic fields at common temperatures (below 120° F./50° C.). Such magnets can be incorporated into flexible fabrics or the like to provide a flexible material suitable for wrapping around joints. By using flexible and/or elastic materials such as NEOPRENE®, a magnetotherapeutic joint wrap previously unseen in the art could be realized.

While certain portions of the human body have been emphasized as being subject to the use of magnetotherapeutic devices, it remains to be seen in the art to provide such magnetotherapy in the form of a mattress pad or the like for joints and/or blood flow in the upper and lower portions of the body with the varying degrees of magnetic polarity. Additionally, strong, magnetic material used in such joint wraps could be used in a mattress pad incorporating such magnetotherapeutic elements. It can be seen, therefore, that it would be of some advantage to provide magnetotherapeutic aid to a person's joints and/or blood flow in the upper and lower portions of the body, particularly while the person rests or sleeps as such magnetotherapeutic treatment could then be effected for a period of several hours without interfering with a person's daily and ongoing activities.

SUMMARY OF THE INVENTION

A magnetic mattress pad providing magnetotherapy while a person rests or sleeps is disclosed herein. The magnetic mattress pad comprises alternating magnetic means in the form of a plurality of uni-pole magnets and triangularboard button magnets. The term "uni-pole magnet" and equivalents used herein are used to indicate a magnet having only one pole (of two) facing the user. As is well known, all magnets have two poles. Magnetic monopoles contradict the currently-known laws of physics (Maxwell's famous equations) and the term "uni-pole" is one of convenience for surface description.

The uni-pole magnets are arranged asymmetrically through the mattress pad while the triangularboard button magnets are located only in the upper portion of the mattress pad. In the upper portion of the mattress pad there are approximately twice as many triangularboard button magnets as there are uni-pole magnets. There are generally more than twice as many uni-pole magnets in the upper portion than in the lower portion of the mattress pad and generally no magnetic means are located in the uppermost portion of the magnetic mattress pad.

Combining the triangularboard button magnets with the uni-pole magnets allow for a stronger magnetic field than using the uni-pole magnets alone. These triangularboard button magnets comprise entire or diagonally-bisected equilateral triangles having opposing north and opposing south poles with Leach of the north poles bounded by a south pole. Each of the triangularboard button magnets may generate approximately 900 Gauss on the surface and 1.5 Gauss at a distance 0.75 inches from the surface. In the preferred embodiment, 200 uni-pole magnets and 234 triangularboard button magnets are present.

OBJECTS OF THE INVENTION

It is an object of the present invention to provide a magnetotherapeutic mattress pad.

It is another object of the present invention to provide magnetotherapy while one rests or sleeps.

It is another object of the present invention to provide highly magnetic magnetotherapy while one rests or sleeps.

These and other objects and advantages of the present invention will be apparent from a review of the following specification and accompanying drawings.

DESCRIPTION OF THE PREFERRED EMBODIMENT(S)

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
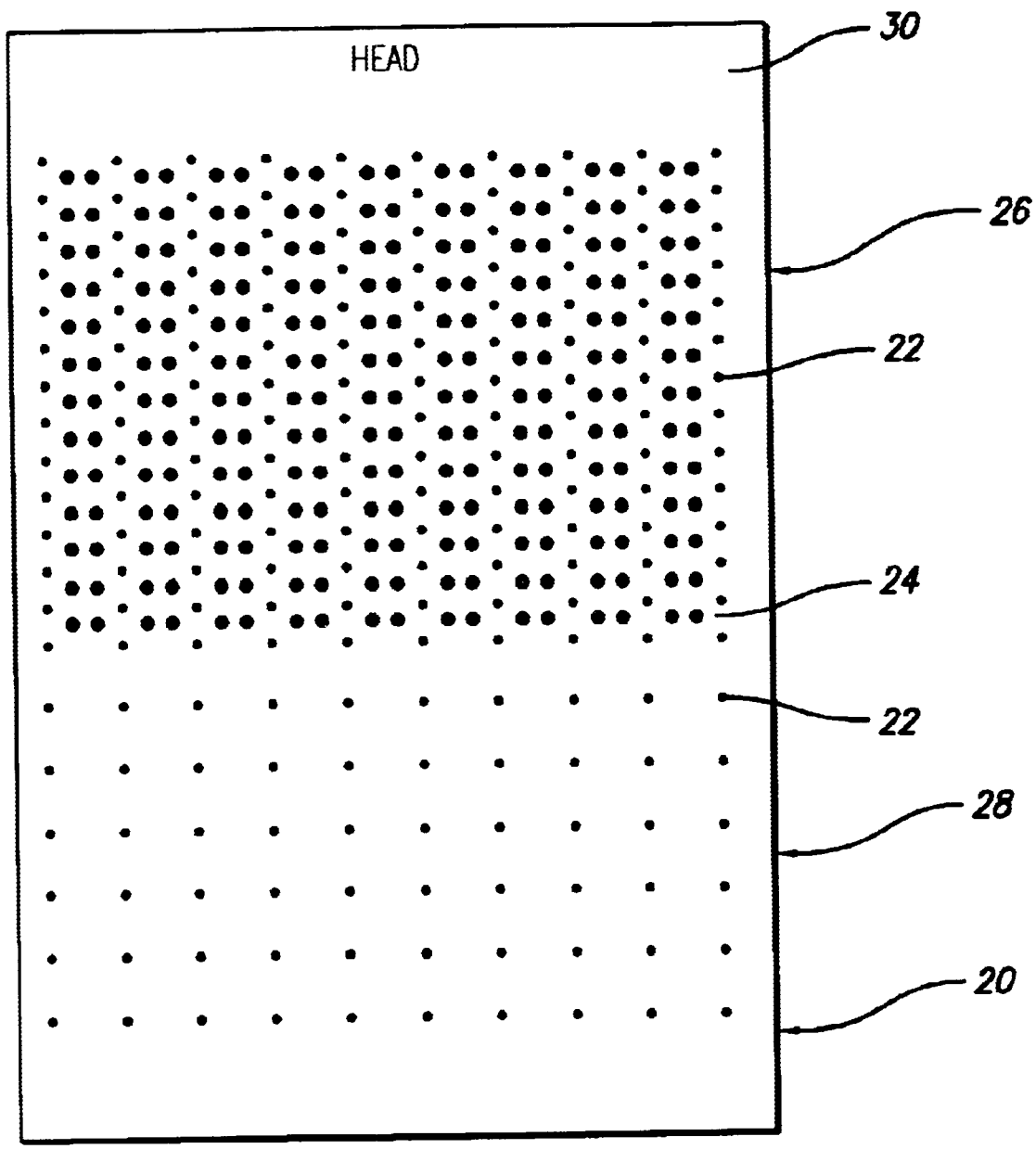
FIG. 1 is a top view of the magnetic mattress pad.

As shown in FIG. 1, a queen size mattress pad 20 is shown according to the construction of the present invention. The smaller dots on the schematic representation of the queen mattress pad 20 indicate uni-pole button magnets 22. A uni-pole magnet or continuous pole magnet is a magnet that has a single pole exposed in a single direction. The other pole faces the other way. The larger dots in the schematic indicate triangularboard button magnets 24 according to the present invention. The triangularboard button magnets 24 generally have a magnetic configuration such as that shown in FIG. 2A.

As can be seen by inspection of FIG. 1, the uni-pole magnets 22 number generally 200 and are distributed across the queen size mattress pad 20 in an asymmetrical fashion. Generally, twice as many uni-pole magnets 22 occur in the top magnetic portion 26 of the pad as opposed to the bottom portion 28 of the pad 20. This asymmetrical distribution generally arises from the preferred application of magnetotherapy to the upper half of a person's body. The torso, including the spinal column and back, provide the greatest access to the predominant, biologically functioning portions of the body. The internal organs such as the liver, heart, stomach, intestines, and back may all benefit through the application of magnetotherapy.

Figure 2A:
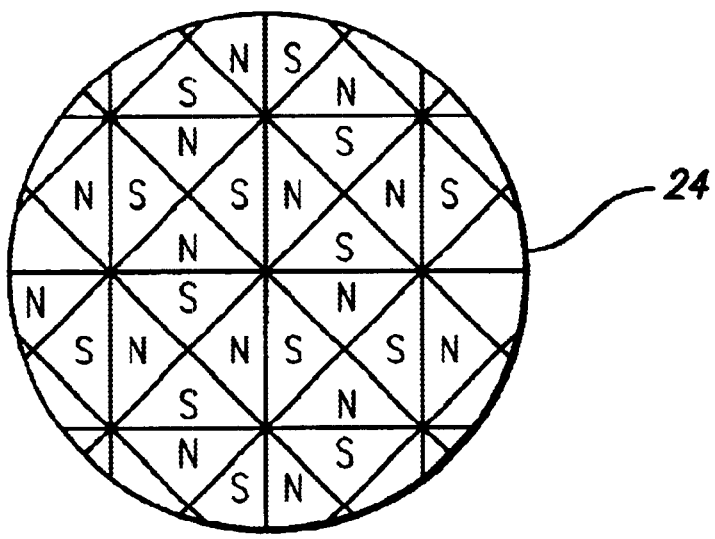
FIG. 2A is a magnified view of the magnetic configuration of an equilateral triangularboard button magnet of the present invention.

The asymmetric distribution of magnetotherapeutic elements is further augmented by the presence of the additional equilateral triangular magnets 24 or other triangular designs only in the upper portion 26 of the pad 20. This provides not only additional magnetotherapy, but also a different form of magnetotherapy to the person reclining on the pad 20. As shown in FIG. 2A, the triangular configuration of alternating magnetic poles provides a plurality of alternating magnetic poles across the face of the triangularly configured magnets 24. While the uni-pole magnets provide only a single pole across their face, the triangularboard button magnets 24 provide a large number of poles across their face depending upon the magnetic configuration of the individual triangularboard button magnet 24.

The asymmetrical distribution of magnetotherapy biased toward the upper portion of a person's body provides greater magnetotherapy for one portion of the person's body. As contemplated in FIG. 1, the person's head is generally anticipated as being adjacent the "head" indicator in FIG. 1. Note should be taken that no magnetotherapeutic elements are present near the uppermost portion of the mattress pad. In this embodiment, the head is left untreated with such magnetotherapy. However, the lower part of the neck, shoulders, torso and upper arms are all subjected to the predominant portion of the magnetotherapy provided by the mattress pad 20. These portions of the body provide the main portion of a person's biological functioning and may advantageously be subject to magnetotherapy. The heart, lungs, liver, back, and shoulders may all be subject to injury, misalignment, or other conditions benefiting advantageously from magnetotherapy. By providing the denser part of the magnetotherapy available from the magnetotherapeutic mattress pad 20 of the present invention, those portions of a person's body often subject to ailment and that may be advantageously subject to magnetotherapy are provided the greater portion of such available magnetotherapy.

The lower extremities are provided magnetotherapy from the uni-pole magnets as shown in the bottom portion 28 of the mattress pad 20. Approximately 60 uni-pole magnets 22 are shown in the lower portion 28 of the pad 20. The remaining 140 uni-pole magnets are all in the upper half 26 of the pad 20, while all 234 triangularboard button magnets 24 are present in the upper portion 26 of the pad 20. As mentioned above, no magnets are present in the topmost portion 30 of the pad 20.

While the uni-pole magnets 22 are equally distributed across the bottom 28 of the mattress pad 20, the same is not similarly true for all magnets in the upper portion 22 of the pad 20. In the upper portion 26 of the mattress pad 20, the uni-pole magnets are all equally distributed. However, the triangularboard button magnets 24 are generally distributed around the square centered upon each uni-pole magnet 22. Consequently, the configuration shown in the upper portion 26 of the pad 20 may be described as follows: a row of ten uni-pole magnets 22 equally spaced and a row of nine in-lying pairs of triangularboard button magnets 24 equally spaced, with the pattern repeated down the upper portion 26 of the pad 20. Other configurations of the triangularboard button magnets 24, for example, different combinations of in-lying pairs and in-lying individual triangularboard button magnets 24 within the row of uni-pole magnets 22 are possible. Also, the denotation of the terms upper and lower is used so as to facilitate the description of the invention and may be used interchangeably according to the distribution of magnetic fields preferred by the user.

Figure 2B:
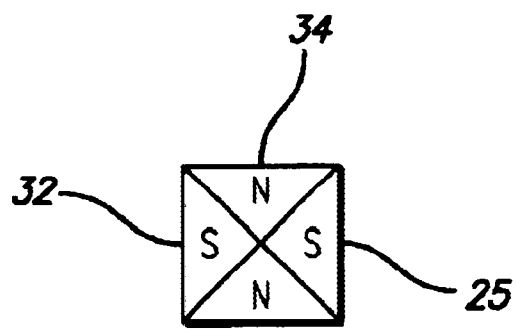
FIG. 2B is a magnified view of a portion of an equilateral triangularboard button magnet of the present invention.
Figure 2C:
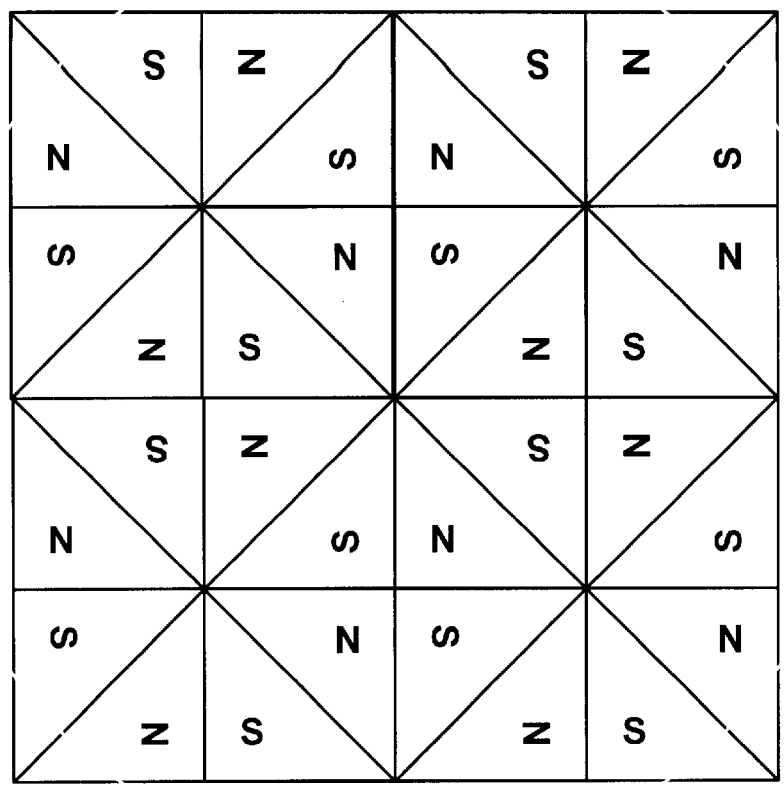
FIG. 2C is a magnified view of the magnetic configuration of an isosceles triangularboard button magnet of the present invention.
Figure 2D:
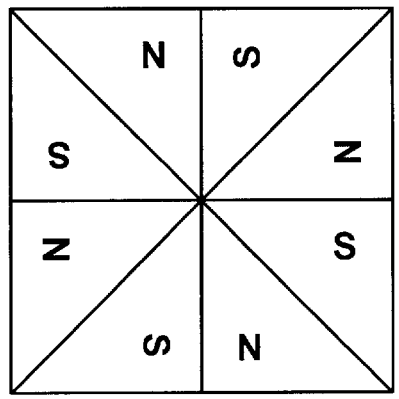
FIG. 2D is a magnified view of a portion of the isosceles triangularboard button magnet of the present invention as shown in FIG. 2C.
Figure 2E:
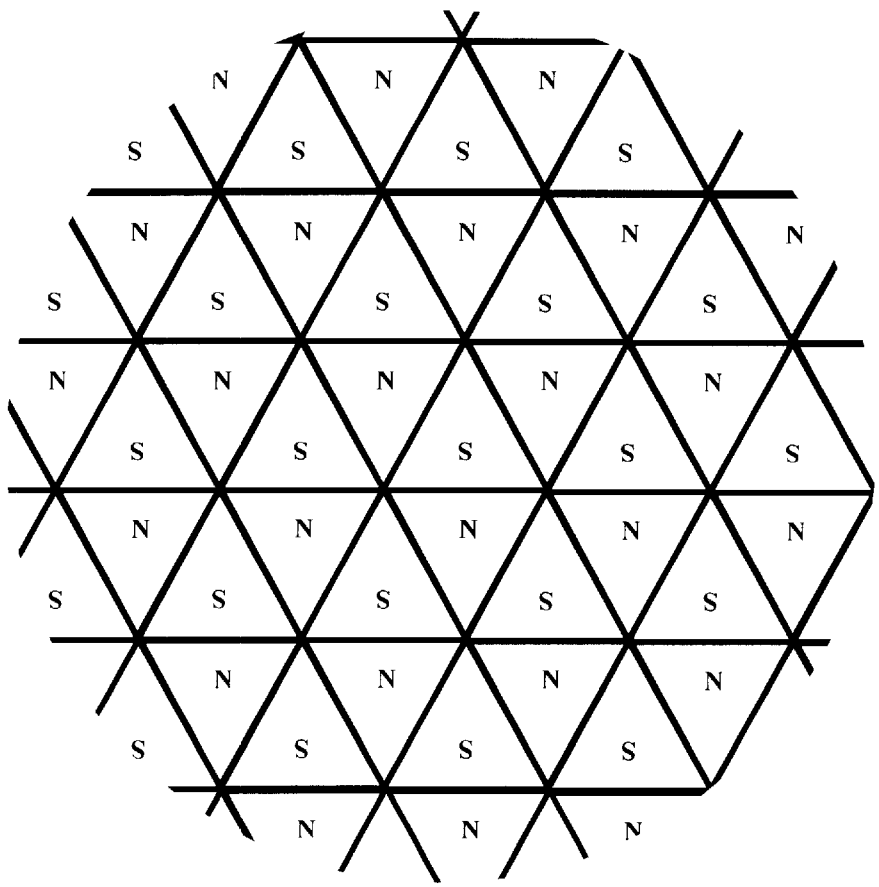
FIG. 2E is a magnified view of a magnetic configuration of an equilateral triangularboard button magnet of the present invention.
Figure 2F:
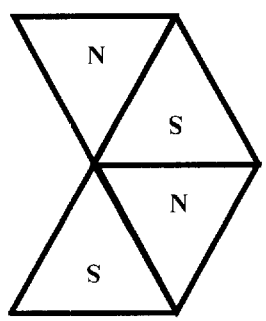
FIG. 2F is a possible unit portion of the equilateral triangularboard button magnet of FIG. 2E.

The triangularboard button magnets 24 may vary in size according to the magnets and are designed as according to FIG. 2A where a diagonally bisected square 25, shown in FIG. 2B, has opposed north poles 32 and opposed south poles 34, with each north pole 32 bounded by a south pole 34 and vice-versa. The triangularboard button magnets 24 provide additional magnetic coverage: with a greater field gradient than provided by the uni-pole magnets 22 alone. Such steep field gradients have been shown to be particularly therapeutic. Some measurements have indicated that the maximum field gradient for the triangularboard button magnets 24 have been approximately 30 milli-Tesla per millimeter.

The triangularboard button magnets 24 may be approximately the same size and shape as the uni-pole button magnets 22, so that they will fit into existing cavities present for such uni-pole magnets 22 and pre-manufactured mattress pads. In some embodiments, the uni-pole button magnets 22 may be approximately $^{11}/_{16}^{th}$ inches in diameter by $^{1}/_{8}^{th}$ inch thick. However, other applications may require different sizes of uni-pole 22 and/or triangularboard button magnets 24.

Triangularboard button magnets 24 (and in some embodiments, the uni-pole magnets may be manufactured using a bonded ferrite injection-molding compound. Energies of such compounds have been found to be 1.8 Mega-Gauss Oerstad (MGOe). When fully magnetized, each button magnet generates approximately 900 Gauss of magnetic field effect on the surface and approximately 1.5 Gauss in a distance of 0.75 inches from the surface of the magnet.

The magnets are designed to be disposed in existing cavities in the foam mattress. The number of magnets incorporated may vary according to specifications indicated by an individual user. More magnets for greater coverage or fewer magnets for less total magnetism may be achieved with the present invention. However, with fewer magnets, there is also less total coverage of area above the mattress pad by magnetotherapeutic magnetism. Magnets may be grouped in certain locations to provide higher density of magnetism. Such groups of higher magnet density may be used to treat specific areas of the body. Additionally, lower magnet density may be provided in areas that are less critical that require less magnetotherapeutic treatment. It should be noted that the size and shape of the magnets allow for exceptional versatility in the magnetic design of any mattress incorporating the present invention.

While the present invention has been described with regards to particular embodiments, it is recognized that additional variations of the present invention may be devised without departing from the inventive concept.

What is claimed is:

1. A magnetic mattress pad, comprising
   an uppermost portion;
   an upper portion including said uppermost portion;
   a lower portion;
   alternating magnetic means for providing changes in magnetic polarity;
   said alternating magnetic means disposed in cavities in said upper portion and said lower portion;
   said alternating magnetic means not located in said uppermost portion;
   said alternating magnetic means comprising a plurality of continuous pole magnets and a plurality of triangularboard button magnets;
   said plurality of continuous magnets are distributed in an asymmetrical fashion;
   said plurality of triangularboard button magnets are located only in said upper portion;
   whereby the magnetic mattress pad provides highly magnetic magnetotherapy while one rests or sleeps.

2. A magnetic mattress pad as set forth in claim 1, wherein said triangularboard button magnets are selected from the group consisting of:
   right-angle triangular magnets, isosceles triangular magnets, and equilateral triangular magnets.

3. A magnetic mattress pad as set forth in claim 1 wherein approximately twice as many of said plurality of continuous pole magnets are located in said upper portion than said lower portion;

approximately twice as many of said plurality of triangularboard button magnets as said plurality of continuous pole magnets are located in said upper portion.

4. A magnetic mattress pad as set forth in claim 3 wherein said plurality of triangularboard button magnets comprise diagonally bisected squares having opposing north poles and opposing south poles, with each of said north poles bounded by said south poles.

5. A magnetic mattress pad as set forth in claim 4, wherein said upper portion comprises a pattern of a row of a plurality of continuous pole magnets equally spaced and a combination of a plurality of in-lying pairs and individual triangularboard button magnets with said pattern repeated down said upper portion.

6. A magnetic mattress pad as set forth in claim 4 wherein said upper portion comprises a pattern of a row of ten of said plurality of continuous pole magnets equally spaced and a row of nine in-lying pairs of said plurality of triangularboard button magnets equally spaced with said pattern repeated down said upper portion.

7. A magnetic mattress pad as set forth in claim 6 wherein each of said plurality of triangularboard button magnets are approximately the same size and shape of said plurality of continuous pole magnets.

8. A magnetic mattress pad as set forth in claim 7, wherein each of said plurality of triangularboard button magnets generate approximately 900 Gauss on the surface and 1.5 Gauss at a distance 0.75 inches from the surface.

9. A magnetic mattress pad as set forth in claim 8, wherein said plurality of continuous pole magnets number generally over 100 and said plurality :of triangularboard button magnets number generally over 100.

10. A magnetic mattress pad as set forth in claim 9, wherein
said plurality of triangularboard button magnets are manufactured using a bond ferrite injection-molding compound.

11. A magnetic mattress pad, comprising
an uppermost portion;
an upper portion including said uppermost portion;
a lower portion;
alternating magnetic means for providing changes in magnetic polarity;
said alternating magnetic means are disposed in cavities in said upper portion and said lower portion;
said alternating magnetic means not located in said uppermost portion;
said alternating magnetic means comprising a plurality of continuous pole magnets and a plurality of triangularboard button magnets;
said plurality of continuous magnets are distributed in an asymmetrical fashion;
said plurality of triangularboard button magnets are located only in said upper portion;
said upper portion comprises a pattern of a row of ten of said plurality of continuous pole magnets equally spaced and an in-lying row of nine of said plurality of triangularboard button magnets equally spaced with said pattern repeated down said upper portion;
whereby the magnetic mattress pad provides highly magnetic magnetotherapy while one rests or sleeps.

12. A magnetic mattress pad, comprising
an uppermost portion;
an upper portion including said uppermost portion;
a lower portion;
alternating magnetic means for providing changes in magnetic polarity;
said alternating magnetic means are disposed in cavities in said upper portion and said lower portion;
said alternating magnetic means not located in said uppermost portion;
said alternating magnetic means comprising a plurality of continuous pole magnets and a plurality of triangularboard.button magnets;
said plurality of continuous magnets distributed in an asymmetrical fashion;
said plurality of triangularboard button magnets located only in said upper portion;
approximately twice as many of said plurality of continuous pole magnets located in said upper portion than said lower portion;
approximately twice as many of said plurality of triangularboard button magnets as said plurality of continuous pole magnets located in said upper portion;
said plurality of triangularboard button magnets comprising diagonally bisected squares having opposing north poles and opposing south poles, with each of said north poles bounded by said south poles;
said upper portion comprises a pattern of a row of ten of said plurality of continuous pole magnets equally spaced and a row of nine in-lying pairs of said plurality of triangularboard button magnets equally spaced with said pattern repeated down said upper portion.

13. A magnetic mattress pad, comprising
an uppermost portion;
an upper portion including said uppermost portion;
a lower portion;
alternating magnetic means for providing changes in magnetic polarity;
said alternating magnetic means are disposed in cavities in said upper portion and said lower portion;
said alternating magnetic means not located in said uppermost portion;
said alternating magnetic means comprising a plurality of continuous pole magnets and a plurality of triangularboard button magnets;
said plurality of continuous magnets are distributed in an asymmetrical fashion;
said plurality of triangularboard button magnets are located only in said upper portion;
approximately twice as many of said plurality of continuous pole magnets located in said upper portion than said lower portion;
approximately twice as many of said plurality of triangularboard button magnets as said plurality of continuous pole magnets located in said upper portion;
said plurality of triangularboard button magnets comprise diagonally bisected squares having opposing north poles and opposing south poles, with each of said north poles bounded by said south poles;
more of said triangularboard button magnets are grouped in certain locations; whereby the magnetic mattress pad provides a higher magnetic density to treat certain areas of the body and a lower magnetic density in less critical areas.

* * * * *